United States Patent
Okamoto et al.

(10) Patent No.: US 10,617,602 B2
(45) Date of Patent: Apr. 14, 2020

(54) COMPOSITION FOR SERUM OR PLASMA SEPARATION, AND CONTAINER FOR BLOOD COLLECTION

(71) Applicant: SEKISUI MEDICAL CO., LTD., Tokyo (JP)

(72) Inventors: Ryusuke Okamoto, Shunan (JP); Kana Hayashi, Shunan (JP); Kuniya Komai, Shunan (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 132 days.

(21) Appl. No.: 15/559,035

(22) PCT Filed: Mar. 31, 2016

(86) PCT No.: PCT/JP2016/060658
§ 371 (c)(1),
(2) Date: Sep. 15, 2017

(87) PCT Pub. No.: WO2016/159236
PCT Pub. Date: Oct. 6, 2016

(65) Prior Publication Data
US 2018/0092806 A1    Apr. 5, 2018

(30) Foreign Application Priority Data
Mar. 31, 2015 (JP) .................. 2015-073883

(51) Int. Cl.
| | | |
|---|---|---|
| A61J 1/05 | (2006.01) | |
| B01L 3/00 | (2006.01) | |
| G01N 33/49 | (2006.01) | |
| G01N 33/50 | (2006.01) | |
| A61K 47/18 | (2017.01) | |
| A61K 47/69 | (2017.01) | |
| A61J 1/14 | (2006.01) | |

(52) U.S. Cl.
CPC .............. *A61J 1/05* (2013.01); *A61K 47/18* (2013.01); *A61K 47/6923* (2017.08); *B01L 3/50* (2013.01); *B01L 3/50215* (2013.01); *G01N 33/491* (2013.01); *G01N 33/5002* (2013.01); *A61J 1/1468* (2015.05)

(58) Field of Classification Search
None
See application file for complete search history.

(56) References Cited

U.S. PATENT DOCUMENTS

| | | | |
|---|---|---|---|
| 5,304,605 A | 4/1994 | Murakami et al. | |
| 5,776,357 A | 7/1998 | Okamoto et al. | |
| 6,447,881 B1 * | 9/2002 | Nishida | B41M 5/5218 |
| | | | 428/32.32 |
| 2007/0138265 A1 | 6/2007 | Powell et al. | |
| 2007/0187341 A1 | 8/2007 | Emerson | |
| 2008/0108493 A1 | 5/2008 | Emerson | |
| 2008/0132874 A1 | 6/2008 | Emerson | |
| 2009/0129973 A1 | 5/2009 | Emerson | |
| 2009/0139937 A1 | 6/2009 | Emerson et al. | |
| 2009/0146099 A1 | 6/2009 | Anraku et al. | |
| 2010/0076223 A1 | 3/2010 | Shiraki et al. | |
| 2010/0108619 A1 | 5/2010 | Emerson | |
| 2010/0117269 A1 | 5/2010 | Emerson | |
| 2010/0267539 A1 | 10/2010 | Emerson | |
| 2010/0314335 A1 | 12/2010 | Emerson | |
| 2011/0262322 A1 | 10/2011 | Emerson | |
| 2012/0070350 A1 | 3/2012 | Anraku et al. | |
| 2012/0234774 A1 | 9/2012 | Emerson | |
| 2012/0308446 A1 | 12/2012 | Inoue et al. | |
| 2013/0143727 A1 | 6/2013 | Emerson | |

(Continued)

FOREIGN PATENT DOCUMENTS

| | | |
|---|---|---|
| CN | 1165558 A | 11/1997 |
| CN | 101454665 A | 6/2009 |

(Continued)

OTHER PUBLICATIONS

Arkema, "Dipropylene glycol diacrylate," pp. 1-5, (2013). (Year: 2013).*
Supplementary European Search Report for the Application No. EP 16 773 116.5 dated Sep. 26, 2018.
International Search Report for the Application No. PCT/JP2016/060658 dated Jun. 21, 2016.

(Continued)

*Primary Examiner* — Randy P Gulakowski
*Assistant Examiner* — Ha S Nguyen
(74) *Attorney, Agent, or Firm* — Cheng Law Group, PLLC

(57) ABSTRACT

There is provided a serum- or plasma-separating composition capable of maintaining stable blood separation performance over a prolonged period even if subjected to a sterilization step during production or to prolonged storage. The serum- or plasma-separating composition comprises a resin composition having fluidity at normal temperature, a silica fine powder, and an amide-based compound represented by the following formula (1):

[Formula 1]

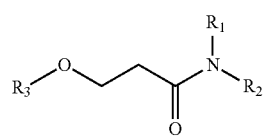

(1)

wherein $R_3$ is an alkyl group having 1 to 4 carbon atoms; and $R_1$ and $R_2$ are independently a hydrogen atom or a linear or branched alkyl group having 1 to 8 carbon atoms.

8 Claims, No Drawings

(56) References Cited

U.S. PATENT DOCUMENTS

| | | | |
|---|---|---|---|
| 2014/0313268 A1* | 10/2014 | Nakano | B41J 11/0015 347/102 |
| 2015/0027957 A1 | 1/2015 | Emerson | |
| 2015/0139868 A1 | 5/2015 | Emerson et al. | |
| 2017/0114234 A1* | 4/2017 | Konda | C09D 11/101 |

FOREIGN PATENT DOCUMENTS

| | | |
|---|---|---|
| CN | 201454557 U | 5/2010 |
| CN | 102770762 A | 11/2012 |
| EP | 2 123 631 A1 | 11/2009 |
| EP | 2 410 329 A1 | 1/2012 |
| JP | 4-340465 A | 11/1992 |
| JP | 5-2014 A | 1/1993 |
| JP | 2012-508578 A | 4/2012 |
| KR | 10-2012-0051939 A | 5/2012 |
| WO | WO-2008/102615 A1 | 8/2008 |
| WO | WO-2011/105151 A1 | 9/2011 |

OTHER PUBLICATIONS

Written Opinion of the International Searching Authority (PCT/USA/237) for Application No. PCT/JP2016/060658 dated Jun. 21, 2016.

Written Opinion of the International Searching Authority (PCT/ISA/237) for Application No. PCT/JP2016/060658 dated Jun. 21, 2016 (English Translation dated Oct. 12, 2017).

The First Office Action for the Application No. 201680006343.6 from The State Intellectual Property Office of the People's Republic of China dated Dec. 14, 2018.

European Office Action for Application No. 16 773 116.5 dated Jan. 20, 2020.

* cited by examiner

COMPOSITION FOR SERUM OR PLASMA SEPARATION, AND CONTAINER FOR BLOOD COLLECTION

TECHNICAL FIELD

The present invention relates to a serum- or plasma-separating composition and to a blood collection container that contains the serum- or plasma-separating composition therein.

BACKGROUND ART

In clinical laboratory tests, blood collection containers are widely used to accommodate blood samples. When a blood collection container that contains a serum- or plasma-separating composition therein is used for blood collection, appropriate adjustment of the specific gravity of the serum- or plasma-separating composition enables centrifugation of a serum component or plasma component from whole blood using of a difference in specific gravities.

The interior of blood collection containers is required to be in a sterilized state by ISO and JIS standards, from the viewpoint of preventing bacterial infection of patients. Thus, sterilization with electron beams, γ rays or the like carried out in the production step, during which changes in the physical properties of the separating composition may be caused. Containers for blood collection are often stored for a prolonged period until use in hospitals. Also in such cases, changes in the physical properties of the separating composition may be caused due to prolonged storage.

When the above changes in the physical properties are caused, there is a known trouble in which a serum component or plasma component cannot be separated from whole blood using a difference in specific gravities even if predetermined centrifugation is conducted. When the centrifuge is small one or old one, which fails to impart desired centrifugal force, this phenomenon would be a more significant problem.

There is a need for a serum- or plasma-separating composition for blood collection containers capable of reducing decrease in the blood separation performance due to changes in the physical properties, even under conditions of storage for a prolonged period as described above.

The following Patent Literature 1 discloses a serum- or plasma-separating composition comprising an acryl-based resin as base material.

The following Patent Literature 2 discloses a serum- or plasma-separating composition comprising polyalkylene glycol added, in response to the above-described problem.

CITATION LIST

Patent Literature

Patent Literature 1: Japanese Patent Laid-Open No. 4-340465
Patent Literature 2: International Publication No. WO 2011/105151 A1

SUMMARY OF INVENTION

Technical Problem

However, the separating composition of Patent Literature 1, in which phase separation occurs during prolonged storage to result in tearing of the separation agent and generation of oil drops on centrifugation, has a problem of failing to form an adequate partition wall.

The separating composition of Patent Literature 2 has a problem of decreasing the thickness of the partition wall during centrifugation when irradiated with γ rays for the purpose of internal sterilization. The separating composition of Patent Literature 2 also has a problem in that setting of the production conditions during actual production is complex because the composition comprises many components.

It is an object of the present invention is to provide a serum- or plasma-separating composition capable of maintaining stable blood separation performance over a prolonged period even if subjected to a sterilization step during production and to prolonged storage, and a blood collection container that contains the serum- or plasma-separating composition therein.

Solution to Problem

The present inventors have intensively studied to found that the above problems can be solved by allowing a serum- or plasma-separating composition to contain a resin composition having fluidity at normal temperature, a silica fine powder, and an amide-based compound represented by the following formula (1).

In other words, the serum- or plasma-separating composition according to the present invention contains a resin composition having fluidity at normal temperature, a silica fine powder, and an amide-based compound represented by the following formula (1):

[Formula 1]

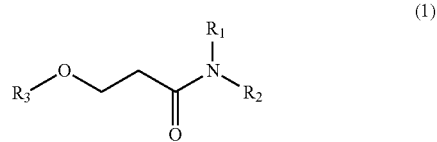

(1)

wherein $R_3$ is an alkyl group having 1 to 4 carbon atoms; and $R_1$ and $R_2$ are independently a hydrogen atom or a linear or branched alkyl group having 1 to 8 carbon atoms.

In another specific aspect of the serum- or plasma-separating composition according to the present invention, the resin composition having fluidity at normal temperature is at least one of a (meth)acrylic acid ester-based polymer or a mixture of a petroleum resin and a trimellitic acid-based plasticizer.

In still another specific aspect of the serum- or plasma-separating composition according to the present invention, the silica fine powder contains hydrophilic silica.

In still another specific aspect of the serum- or plasma-separating composition according to the present invention, the content of the hydrophilic silica is in the range of 1.40 to 2.00% by weight.

In still another specific aspect of the serum- or plasma-separating composition according to the present invention, the content of the amide-based compound is in the range of 0.10 to 0.35% by weight.

In still another specific aspect of the serum- or plasma-separating composition according to the present invention, hydrophobic silica is contained in addition to the hydrophilic silica.

In still another specific aspect of the serum- or plasma-separating composition according to the present invention, the total content of the hydrophobic silica and the hydrophilic silica is in the range of 1.40 to 2.50% by weight.

In still another specific aspect of the serum- or plasma-separating composition according to the present invention, the specific gravity of the serum- or plasma-separating composition is from 1.038 to 1.045.

The blood collection container according to the present invention contains a serum- or plasma-separating composition constituted according to the present invention therein.

Advantageous Effects of Invention

According to the present invention, phase separation caused when a blood collection container is stored for a prolonged period can be prevented, and thus reversible overtime changes can be reduced. Changes in the yield value when γ-ray sterilization is conducted also can be reduced. Accordingly, the blood collection container that contains the serum- or plasma-separating composition therein of the present invention can maintain stable blood separation performance over a prolonged period as well as can prevent occurrence of oil drops due to tearing of the serum- or plasma-separating composition on centrifugation and clogging of the probe due to the occurrence of oil drops.

According to the present invention, the serum- or plasma-separating composition can be produced with a lesser amount of raw materials than before. Accordingly, the production conditions are easily controlled and stable production is enabled.

DESCRIPTION OF EMBODIMENT

The details of the present invention will be described hereinafter.

The serum- or plasma-separating composition according to the present invention comprises a resin composition having fluidity at normal temperature, a silica fine powder, and an amide-based compound represented by the following formula (1):

[Formula 2]

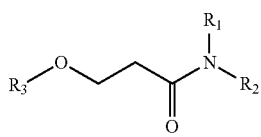
(1)

wherein $R_3$ is an alkyl group having 1 to 4 carbon atoms; and $R_1$ and $R_2$ are independently a hydrogen atom or a linear or branched alkyl group having 1 to 8 carbon atoms.

Thus, the serum- or plasma-separating composition according to the present invention can maintain stable blood separation performance over a prolonged period even if subjected to a sterilization step during production and to prolonged storage. The above-described $R_1$ and $R_2$ may be each identical or different.

<Resin Composition Having Fluidity at Normal Temperature>

The serum- or plasma-separating composition of the present invention contains a resin composition having fluidity at normal temperature. Examples of the resin composition having fluidity at normal temperature include (meth)acrylic acid ester-based polymers and mixtures of a petroleum resin and a trimellitic acid-based plasticizer. These may be used singly, or two or more of these may be used in combination.

No particular limitation is placed on constituent monomers of an acryl-based resin provided that the monomers are common ones. Those obtained by random-copolymerizing or block-copolymerizing monomer components such as methyl acrylate, 2-ethylhexyl acrylate, and butyl acrylate are used, without particular limitation. For the purpose of improving the temperature dependency of the resin viscosity, styrene may be copolymerized. The normal temperature used herein represents 20±5° C. according to the Japanese Pharmacopoeia.

The above-described (meth)acrylic acid ester-based polymer is obtained by polymerizing raw material comprising at least one (meth)acrylic acid ester monomer. The raw material may contain monomers other than the (meth)acrylic acid ester. In other words, the (meth)acrylic acid ester-based polymer may be a homopolymer of one (meth)acrylic acid ester monomer, may be a copolymer comprising two or more of (meth)acrylic acid ester monomers, or may be a copolymer comprising at least one (meth)acrylic acid ester monomer and a monomer other than the (meth)acrylic acid ester monomer.

The content of the (meth)acrylic acid ester monomer in the above-described (meth)acrylic acid ester-based polymer is preferably 50 to 100% by weight, more preferably 60 to 100% by weight, still more preferably 70 to 100% by weight.

By setting the content of the (meth)acrylic acid ester monomer to 50% by weight or more, the balance between the specific gravity, thixotropy, and fluidity of the polymer for the blood separating agent can be maintained still more satisfactorily. In the case of the above-described preferable range, the balance of these can be still more improved.

Examples of the above-described (meth)acrylic acid ester monomer include (meth)acrylic acid alkyl esters comprising an alkyl group having 1 to 20 carbon atoms, (meth)acrylic acid polyalkylene glycol esters, (meth)acrylic acid alkoxyalkyl esters, (meth)acrylic acid hydroxyalkyl esters, (meth)acrylic acid glycidyl esters, (meth)acrylic acid dialkylaminoalkyl esters, (meth)acrylic acid benzyl esters, (meth)acrylic acid phenoxyalkyl esters, (meth)acrylic acid cyclohexyl esters, (meth)acrylic acid isobornyl esters, and (meth)acrylic acid alkoxysilylalkyl esters.

One of the above-described monomers or two or more of the above-described monomers can be appropriately used as a raw material constituent of the (meth)acrylic acid ester-based polymer. Two or more of the (meth)acrylic acid ester monomers are desirably used. When two or more of the monomers are used, the (meth)acrylic acid ester-based polymer can be easily controlled to have a desired specific gravity and viscosity by adjusting the content ratio between the two or more monomers having different molecular structures.

No particular limitation is placed on the monomer other than the above-described (meth)acrylic acid ester monomer, provided that the monomer is a radical-polymerizable monomer capable of being radical-copolymerized with a (meth)acrylic acid alkyl ester.

Examples of such a radical-polymerizable monomer include aromatic vinyl monomers, vinyl esters, vinyl ethers, vinyl pyrrolidone, and (meth)allyl ethers.

Examples of the aromatic vinyl monomer include styrene, α-methylstyrene, p-methylstyrene, α-methyl-p-methylstyrene, p-methoxystyrene, o-methoxystyrene, 2,4-dimethylstyrene, chlorostyrene, and bromostyrene. Examples of the vinyl ester include (meth)acrylate, maleate anhydride, fumarate, (meth)acrylamide, dialkyl(meth)acrylamide, and vinyl acetate. One or two or more of the above-described radical-polymerizable monomers can be appropriately used.

The above-described radical-polymerizable monomer is preferably an aromatic vinyl monomer, more preferably styrene or α-methylstyrene. Aromatic vinyl monomers have a high specific gravity and high hydrophobicity and are therefore effective in further reducing adsorption of a blood separating agent while maintaining the blood separation performance of the agent. Furthermore, a copolymer obtained by copolymerization of the above-described aromatic vinyl monomer and a (meth)acrylic acid ester monomer is less likely to have an increase in the molecular weight during sterilization by radiation, and thus less likely to an increase in the viscosity, as compared with (meth)acrylic acid ester-based polymers containing no aromatic vinyl monomer described above.

The content of the above-described aromatic vinyl monomer in the monomer composition for obtaining the above-described (meth)acrylic acid ester-based polymer is preferably 1% by weight or more and less than 50% by weight, more preferably in the range of 5 to 30% by weight, and still more preferably in the range of 10 to 20% by weight. When the content of the aromatic vinyl monomer is less than 1% by weight, the effect due to the use of the aromatic vinyl monomer may not be satisfactorily achieved. In contrast, when the content of the aromatic vinyl monomer is 50% by weight or more, the viscosity of the (meth)acrylic acid ester-based polymer will be excessively high, and thus moderate fluidity becomes difficult to obtain.

The above-described (meth)acrylic acid ester-based polymer can be obtained by an ordinary radical polymerization process. Examples of the radical polymerization process include a solution polymerization process, a bulk polymerization process, a dispersion polymerization process, and a living radical polymerization process.

The weight-average molecular weight (Mw) of the above-described (meth)acrylic acid ester-based polymer is preferably in the range of 3,000 to 50,000, more preferably in the range of 4,000 to 30,000. When the weight-average molecular weight is in the above-described ranges, the fluidity of the blood separating agent can be more satisfactory, and the strength of the partition wall to be formed can be further improved. When the weight-average molecular weight is less than 3,000, the strength of the partition wall may become insufficient. Alternatively, suspended matter may form in serum or plasma to have an adverse effect on test values or contaminate precise analytical equipment. When the weight-average molecular weight exceeds 50,000, the fluidity during centrifugation will be reduced. This may prevent reliable formation of a partition wall between clots and serum or between blood cell components and plasma.

No particular limitation is placed on the mixture of a petroleum resin and a trimellitic acid-based plasticizer provided that the petroleum resin is a common one, and examples thereof include mixtures prepared by melting and mixing a polymer of cyclopentadiene oligomers and a plasticizer under heating so as to achieve a desired viscosity.

No particular limitation is placed on the above-described cyclopentadiene oligomer, and examples thereof include polymers of cyclopentadiene monomers such as hydrogenated products of polymers of at least one monomer selected from cyclopentadiene, dicyclopentadiene, and alkyl substituted derivatives of cyclopentadiene. Examples of such a cyclopentadiene oligomer include ESCOREZ 5380, ESCOREZ 5300, ESCOREZ 5320, ESCOREZ 5340, ESCOREZ 5400, and ESCOREZ ECR251 (all manufactured by Exxon Mobil Corporation).

Hydrogenated products of copolymers of at least one of the above-described cyclopentadiene monomers and at least one aromatic monomer selected from styrene, methylstyrene, indene, and methylindene also can be used. Examples thereof include ESCOREZ® ECR227E, ESCOREZ ECR235E, ESCOREZ ECR231C, ESCOREZ 5690, and ESCOREZ 5600 (all manufactured by Exxon Mobil Corporation).

As the plasticizer used in the present invention, phthalic acid esters, trimellitic acid esters, and pyromellitic acid esters, which are aromatic ester compounds, can be used. Of these, trimellitic acid esters and pyromellitic acid esters are suitably used.

The trimellitic acid esters or pyromellitic acid esters used in the present invention belong to aromatic ester compounds, as with phthalic acid esters, and are not particularly limited provided that the ester is an ester of trimellitic acid or an ester of pyromellitic acid. Examples of the trimellitic acid ester or pyromellitic acid ester include alkyl esters of trimellitic acid or alkyl esters of pyromellitic acid, specifically, tri-n-octyl trimellitate, triisooctyl trimellitate, triisodecyl trimellitate, and tetraisooctyl pyromellitate. The trimellitic acid ester and pyromellitic acid ester may be used singly or may be mixed and used.

Example of the alkyl ester of the above-described trimellitic acid or pyromellitic acid include MONOCIZER® W-700 (triisooctyl trimellitate), MONOCIZER W-750 (tri-n-octyl trimellitate), and MONOCIZER W-7010 (tetraisooctyl pyromellitate) manufactured by DIC Corporation and SANSO CIZER® TOTM (triisooctyl trimellitate) and SANSO CIZER TITM (triisodecyi trimellitate) manufactured by New Japan Chemical Co., Ltd.

In order to form a partition wall that exhibits sufficient performance at low temperatures or even when centrifugal force is low, in an intermediate layer between clots (specific gravity: 1.08) and serum (specific gravity: 1.03) or between blood cell components (specific gravity: 1.08) and plasma (specific gravity: 1.03), the specific gravity of the serum- or plasma-separating composition at 25° C. is preferably 1.038 to 1.045.

Therefore, the specific gravity of the above-described resin composition having fluidity at normal temperature at 25° C. is preferably in the range of 1.030 to 1.040, more preferably in the range of 1.030 to 1.034. When the specific gravity is less than 1.030, addition of a large amount of the silica fine powder may be needed in order to adjust the specific gravity of the serum- or plasma-separating composition within the above-described range. As a result, the inorganic powder and the polymer for the blood separating agent are separated from each other by centrifugation, or the blood separating agent absorbs moisture during prolonged storage. Thus, the hydrogen bonding strength between the inorganic powder particles may increase, which may reduce the fluidity of the blood separating agent. Accordingly, there may arise a problem in that a partition wall in the intermediate layer between clots and serum or between blood cell components and plasma cannot be formed. In contrast, when the specific gravity is more than 1.040, addition of a silica fine powder necessary to give thixotropy to the polymer for the blood separating agent excessively increases the specific gravity of the blood separating agent. This may prevent formation of a partition wall in an intermediate layer between clots and serum or between blood cell components and plasma.

The viscosity of the above-described resin composition having fluidity at normal temperature at 25° C. is preferably 10 to 200 Pa·s, more preferably 30 to 150 Pa·s. When the viscosity is in the above ranges, the fluidity of the blood separating agent can be increased to maintain the strength of the resultant partition wall. When the above viscosity is less than 10 Pa·s, the strength of the partition wall may be insufficient or suspended matter may form in serum or plasma to have an adverse effect on test values or contaminate precise analytical equipment. When the above viscosity exceeds 200 Pa·s, the fluidity during centrifugation can be decreased and reliable formation of a partition wall between clots and serum or between blood cell components and plasma may be prevented.

<Silica Fine Powder>

The serum- or plasma-separating composition of the present invention contains a silica fine powder.

Examples of the silica fine powder include natural silica and synthetic silica, which are not particularly limited provided that the silica is mainly based on silicon dioxide. Synthetic silica produced by a gas phase process is preferable because of its stable quality. Examples of such synthetic silica include hydrophilic silica and hydrophobic silica.

Hydrophilic silica, in which hydroxy groups on the surface of the particles are hydrogen-bonded to each other, imparts thixotropy to the serum- or plasma-separating composition, and additionally has an effect of adjusting the specific gravity. In contrast, hydrophobic silica, in which hydroxy groups on the surface of the particles are substituted by hydrophobic groups such as methylsilane and thus do not form hydrogen bonding, only has an effect of adjusting the specific gravity. When both the specific gravity of the serum- or plasma-separating composition and the thixotropy cannot be maintained within a suitable range only with the above-described hydrophilic silica, hydrophilic silica and hydrophobic silica may be used in combination as appropriate in order to suitably adjust the thixotropy and the specific gravity of serum- or plasma-separating composition separately.

The total content of the hydrophilic silica and the hydrophobic silica (the sum of the content of the hydrophilic silica and the content of the hydrophobic silica) is preferably in the range of 1.40 to 2.50% by weight in order to allow both the specific gravity and the thixotropy of the serum- or plasma-separating composition to be in a suitable range. More preferably, both the silicas are used in the range of 1.45 to 2.15% by weight. In a specific method, the content of the hydrophilic silica is specified such that the thixotropy of the serum- and plasma-separating composition falls within a suitable range. When the specific gravity of the serum- or plasma-separating composition falls below the suitable range, with the specified content, the composition is generally allowed to further contain hydrophobic silica in the amount corresponding to the content lacking. For evaluation of thixotropy, various known methods are known. For evaluation of the serum- or plasma-separating composition, flowing evaluation described later is suitable.

The content of the hydrophilic silica is preferably in the range of 1.40 to 2.00% by weight. More preferably the hydrophilic silica is used in the range of 1.45 to 1.85% by weight.

Of silica fine powders, as the hydrophilic silica, for example, hydrophilic silica produced by a gas phase process including AEROSIL series such as AEROSIL® 90G, 130, 200, and 300 (manufactured by NIPPON AEROSIL CO., LTD.), REOLOSIL series such as REOLOSIL® QS-10, QS-20, and QS-30 (manufactured by Tokuyama Corporation), and WACKERHDK series such as WACKERHDK S13, N20, and T30 (manufactured by Wacker Asahikasei Silicone Co., Ltd.) are available and easily used.

As the hydrophobic silica, for example, hydrophobic silica produced by a gas phase process including AEROSIL series such as AEROSIL R972, R974, R805, and R812 (manufactured by NIPPON AEROSIL CO., LTD.), REOLOSIL series such as REOLOSIL MT-10, DM-30S, HM-30S, KS-20S, and PM-20 (manufactured by Tokuyama Corporation), and WACKERHDK series such as WACKERHDK H15, H18, and H30 (manufactured by Wacker Asahikasei Silicone Co., Ltd.) are easily available and used. The hydrophobic silica, which is to be contained for adjustment of the specific gravity of the serum- or plasma-separating composition, is a component having a high specific gravity and exerts no negative influence on blood. Any materials that can be kneaded homogeneously, which is not particularly limited to hydrophobic silica, may be used, such as alumina, glass fine powder, talc, kaolin, bentonite, titania, and zirconium.

<Amide-Based Compound>

The serum- or plasma-separating composition of the present invention contains an amide-based compound.

No particular limitation is placed on the amide-based compound used in the serum- or plasma-separating composition of the present invention provided that the compound satisfies the following formula (1). Particularly when $R_3$ is a methyl group, the compound exerts the maximum effect. No particular limitation is placed on the linear or branched alkyl group that can apply to $R_1$ and $R_2$ provided that the alkyl group has 1 to 8 carbon atoms. Examples thereof include a methyl group, an ethyl group, an n-propyl group, an isopropyl group, an n-butyl group, a sec-butyl group, a tert-butyl group, a pentyl group, a hexyl group, a heptyl group, and an octyl group.

[Formula 3]

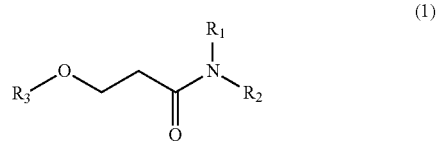

(1)

wherein $R_3$ is an alkyl group having 1 to 4 carbon atoms; and $R_1$ and $R_2$ are independently a hydrogen atom or a linear or branched alkyl group having 1 to 8 carbon atoms.

In above formula (1), $R_1$ and $R_2$ may be each identical or different. Amide-based compounds disperse the silica fine powder homogeneously in the resin composition to stabilize the hydrogen bonds formed between hydroxyl groups on the surface of the silica fine powder particles, and consequently, have an effect of stabilizing the thixotropy of the serum- or plasma-separating composition by reducing its overtime changes.

An excessively small or large amount of the amide-based compound used in the present invention fails to stabilize the thixotropy of the serum- or plasma-separating composition. Consequently, sufficient blood separation performance may not be exerted. Thus, the amide-based compound used in the present invention is added preferably in the range of 0.10 to 0.35% by weight, more preferably in the range of 0.15 to 0.30% by weight based on the whole composition.

The amide-based compound suitably used in the present invention can be produced by the method described in WO 2008/102615 A1 or in Japanese Patent Laid-Open No. 2005-47885. Commercially available examples thereof include Equamide® (manufactured by Idemitsu Kosan Co., Ltd.) M100 and B100.

<Other Components>

In addition to those described above, the serum- or plasma-separating composition of the present invention may comprise various components within the range in which the performance as a separating composition for blood collection containers intended by the present invention can be maintained. Specific examples thereof include an antioxidant and a colorant.

<Production Method>

No particular limitation is placed on the method for producing the serum- or plasma-separating composition of the present invention. For example, a resin composition having fluidity at normal temperature, a silica fine powder, and an amide-based compound may be mixed together homogeneously. No particular limitation is placed on the mixing process, and any known mixer, such as a planetary mixer, a ball mill, or a disperser is used.

<Application to Blood Collection Container>

The blood collection container according to the present invention contains a serum- or plasma-separating composition constituted according to the present invention therein.

No particular limitation is placed on the shape of the above-described blood collection container. Preferably, the container is a bottomed cylindrical container, for example.

No particular limitation is placed on the materials of the above-described blood collection container. Any known material can be used, for example, thermoplastic resins such as polyethylene, polypropylene, polystyrene, polyethylene terephthalate, polymethyl methacrylate, polyacrylonitrile, polyamide, acrylonitrile-styrene copolymers, and ethylene-vinyl alcohol copolymers; thermosetting resins such as unsaturated polyester resins, epoxy resins, and epoxy-acrylate resins; modified natural resins such as cellulose acetate, cellulose propionate, ethyl cellulose, and ethylchitin; silicates such as soda-lime glass, phosphosilicate glass, and borosilicate glass, glasses such as quartz glass, combinations thereof, and materials mainly composed thereof. Depending on the purpose, such as prevention of blood sticking and acceleration of blood coagulation, any known agent such as a blood coagulation accelerator may be allowed to stick on the tube wall.

No particular limitation is placed on the inner pressure of the blood collection container. The container also can be used as a so-called vacuum blood collection tube, which is sealed with a sealing member such as a plug and an aluminum seal and the interior of which is evacuated. In the case of a vacuum blood collection tube, a predetermined amount of blood can be easily collected irrespective of the skills of the blood collecting operator. The interior of the blood collection tube is desirably sterilized in compliance with the criteria described in JIS or ISO, from the viewpoint of infection prevention.

Hereinafter, the present invention will become apparent by reference to specific examples of the invention and comparative examples. Note that the present invention is not limited to the following examples.

Examples 1 to 21, Reference Examples 1 to 5, and Comparative Examples 1 and 2

The material compositions of the serum- or plasma-separating compositions used in Examples 1 to 21, Reference Examples 1 to 5, and Comparative Examples 1 and 2 are shown in Table 1 below. Performance evaluation of the blood collection containers used in Examples 1 to 21, Reference Examples 1 to 5, and Comparative Examples 1 and 2 are shown in Table 2 below. Compounds used as a component to be blended of the serum- or plasma-separating compositions in Examples 1 to 21, Reference Examples 1 to 5, and Comparative Examples 1 and 2 are as shown in Table 1, and more specifically are as follows.

<(Meth)Acrylic Acid Ester-Based Polymer>

In the presence of an azo polymerization initiator, 2-ethylhexyl acrylate and butyl acrylate were radical-polymerized by a solution process to obtain a polymer. The polymer had a weight-average molecular weight of 20,000, a viscosity at 25° C. of 74 Pa-s, and a specific gravity at 25° C. of 1.031.

<Petroleum Resin>

Product names "ESCOREZ 5380" and "ESCOREZ 5400" manufactured by Exxon Mobil Corporation were used.

<Plasticizer>

Product name "MONOCIZER W-700 (triisooctyl trimellitate)" manufactured by DIC Corporation was used.

<Silica Fine Powder>

Product name "200CF" manufactured by NIPPON AEROSIL CO., LTD. as the hydrophilic silica and product name "R974" manufactured by NIPPON AEROSIL CO., LTD. as the hydrophobic silica were used.

<Amide-Based Compound>

Product name "Equamide M100 (3-methoxy-N,N-dimethylpropaneamide)" manufactured by Idemitsu Kosan Co., Ltd. was used.

<Gelling Agent>

Product name "GEL ALL D (dibenzylidene sorbitol)" manufactured by New Japan Chemical Co., Ltd. and N-methylpyrrolidone manufactured by BASF SE were mixed in a weight ratio of 1:4 to form a homogeneous solution before use.

Product name "NEWPOL PE-71 (polyoxyethylene polyoxypropylene glycol)" manufactured by Sanyo Chemical Industries, Ltd. and product name "PREMINOL S3011 (polyoxypropylene glyceryl ether)" manufactured by NOF CORPORATION were used.

In Examples, Reference Examples, and Comparative Examples, the compounds shown above were weighed according to the blend compositions shown in the Table 1 below into a 500 mL kneading vessel such that the total weight reached 100 g. The weighed compounds were kneaded at room temperature under vacuum for 12 minutes using a planetary mixer to prepare serum- or plasma-separating compositions. In Example 11 and Comparative Example 1, the above-described petroleum resin and plasticizer were used as the resin composition having fluidity at normal temperature. In all the other Examples, Reference Examples, and Comparative Examples, the above-described (meth)acrylic acid ester-based polymer was used as the resin composition having fluidity at normal temperature. In Comparative Examples 1 and 2, an amide-based compound was not used.

In the case of using a resin composition having fluidity at normal temperature comprising a petroleum resin and a plasticizer, both the components were melted and mixed in a glass vessel preheated to 120° C. before use. A blood collection container was prepared by placing 1.0 mL of the serum- or plasma-separating composition prepared in the bottom of a bottomed PET tube having an inner diameter of 16 mm and a length of 100 mm. The following evaluation was carried out using the blood collection container prepared.

<Viscosity>

The viscosity of 0.5 mL of the serum- or plasma-separating composition at a shear rate of 1.0 second$^{-1}$ and 25° C. was measured with an E-type viscometer (manufactured by Toki Sangyo Co., Ltd., product number "TVE-35").

<Specific Gravity>

One drop of the serum- or plasma-separating composition was added sequentially in a plurality of saline solutions at 25° C. having a specific gravity adjusted in a stepwise manner with an increment of 0.002, and the specific gravity was determined by floating and sinking in the saline solutions.

<Flowing>

The opening end of the blood collection container was held facing obliquely downward at 450 and left to stand in an oven warmed at 55° C. for 24 hours. The distance for which the serum- or plasma-separating composition flowed downward along the inner wall of the bottomed PET tube was measured with a vernier caliper.

<Partition Wall Thickness>

The blood collection container was filled with 2.5 mL of a saline solution at 25° C. having a specific gravity of 1.065 and cooled in a water bath at 15° C. for 30 minutes. Subsequently, the solution was centrifuged in a centrifuge kept at 15° C. under conditions of 1700 G and five minutes. The thickness of the partition wall of the serum- or plasma-separating composition formed on the saline solution was measured with a vernier caliper.

TABLE 1

| | Resin composition having fluidity at normal temperature (% by weight) | | Silica fine powder (% by weight) | | Amide-based compound | Gelling agent (% by weight) | | |
|---|---|---|---|---|---|---|---|---|
| | (Meth)acrylic acid ester-based polymer | Mixture of petroleum resin and trimellitic acid-based plasticizer | 200CF | R974 | Equamide M100 (% by weight) | Mixture of GEL ALL D and N-methylpyrrolidone | NEWPOL PE-71 | PREMINOL S3011 |
| Example 1 | 98.40 | — | 1.45 | 0.00 | 0.15 | — | — | — |
| Example 2 | 98.35 | — | 1.50 | 0.00 | 0.15 | — | — | — |
| Example 3 | 97.55 | — | 1.55 | 0.75 | 0.15 | — | — | — |
| Example 4 | 98.25 | — | 1.60 | 0.00 | 0.15 | — | — | — |
| Example 5 | 97.55 | — | 1.70 | 0.60 | 0.15 | — | — | — |
| Example 6 | 97.95 | — | 1.90 | 0.00 | 0.15 | — | — | — |
| Example 7 | 97.75 | — | 1.90 | 0.20 | 0.15 | — | — | — |
| Example 8 | 97.55 | — | 1.90 | 0.40 | 0.15 | — | — | — |
| Example 9 | 98.00 | — | 1.40 | 0.40 | 0.20 | — | — | — |
| Example 10 | 98.35 | — | 1.45 | 0.00 | 0.20 | — | — | — |
| Example 11 | — | 98.35 | 1.45 | 0.00 | 0.20 | — | — | — |
| Example 12 | 98.30 | — | 1.50 | 0.00 | 0.20 | — | — | — |
| Example 13 | 98.00 | — | 1.50 | 0.30 | 0.20 | — | — | — |
| Example 14 | 98.25 | — | 1.55 | 0.00 | 0.20 | — | — | — |
| Example 15 | 98.20 | — | 1.60 | 0.00 | 0.20 | — | — | — |
| Example 16 | 98.00 | — | 1.80 | 0.00 | 0.20 | — | — | — |
| Example 17 | 98.25 | — | 1.45 | 0.00 | 0.30 | — | — | — |
| Example 18 | 98.20 | — | 1.50 | 0.00 | 0.30 | — | — | — |
| Example 19 | 97.90 | — | 1.50 | 0.30 | 0.30 | — | — | — |
| Example 20 | 98.15 | — | 1.55 | 0.00 | 0.30 | — | — | — |
| Example 21 | 98.10 | — | 1.60 | 0.00 | 0.30 | — | — | — |
| Reference Example 1 | 98.55 | — | 1.40 | 0.00 | 0.05 | — | — | — |
| Reference Example 2 | 98.05 | — | 1.30 | 0.50 | 0.15 | — | — | — |
| Reference Example 3 | 97.15 | — | 1.90 | 0.80 | 0.15 | — | — | — |
| Reference Example 4 | 97.55 | — | 2.10 | 0.20 | 0.15 | — | — | — |
| Reference Example 5 | 98.15 | — | 1.45 | 0.00 | 0.40 | — | — | — |
| Comparative Example 1 | — | 97.00 | 1.17 | 1.73 | — | 0.10 | — | — |
| Comparative Example 2 | 96.35 | — | 1.17 | 1.73 | — | — | 0.25 | 0.50 |

TABLE 2

| | Specific gravity | Viscosity (Pa·s) | Flowing (mm) | Partition wall thickness (mm) |
|---|---|---|---|---|
| Example 1 | 1.041 | 135 | 2.91 | 5.84 |
| Example 2 | 1.041 | 137 | 2.53 | 5.65 |
| Example 3 | 1.045 | 156 | 3.39 | 4.67 |
| Example 4 | 1.041 | 142 | 2.84 | 4.9 |
| Example 5 | 1.045 | 160 | 2.54 | 4.71 |
| Example 6 | 1.043 | 196 | 0.87 | 5.02 |
| Example 7 | 1.044 | 179 | 1.65 | 6.27 |
| Example 8 | 1.045 | 197 | 0.38 | 3.97 |
| Example 9 | 1.043 | 154 | 4.69 | 4.9 |
| Example 10 | 1.041 | 149 | 3.58 | 5.54 |
| Example 11 | 1.041 | 235 | 5.12 | 4.07 |
| Example 12 | 1.041 | 156 | 2.3 | 5.54 |
| Example 13 | 1.042 | 159 | 3.13 | 4.56 |
| Example 14 | 1.041 | 158 | 4.82 | 5.23 |
| Example 15 | 1.041 | 160 | 2.8 | 5.3 |
| Example 16 | 1.043 | 166 | 2.1 | 4.45 |
| Example 17 | 1.041 | 170 | 5.43 | 5.08 |
| Example 18 | 1.042 | 192 | 3.31 | 4.54 |
| Example 19 | 1.041 | 156 | 2.26 | 5.18 |
| Example 20 | 1.041 | 186 | 3.23 | 4.68 |
| Example 21 | 1.041 | 197 | 2.49 | 4.55 |
| Reference Example 1 | 1.04 | 127 | 8.5 | 5.9 |
| Reference Example 2 | 1.043 | 147 | 7.19 | 5.27 |
| Reference Example 3 | 1.046 | 175 | 0.47 | 3.5 |
| Reference Example 4 | 1.045 | 211 | 0.15 | 3.86 |
| Reference Example 5 | 1.01 | 191 | 7.45 | 4.85 |
| Comparative Example 1 | 1.049 | 205 | 10.24 | 0.48 |
| Comparative Example 2 | 1.045 | 199 | 12.8 | 3.13 |

As clearly seen from Table 2, the serum- or plasma-separating compositions shown in Examples 1 to 21 exhibited satisfactory results in all the evaluation points including "viscosity", "flowing", and "partition wall thickness".

In Reference Examples 1, 2, and 5, with respect to the evaluation point "flowing", flowing of the separating composition slightly occurs. Thus, it may not be possible to maintain the thixotropy over a prolonged period due to overtime changes. In Reference Examples 3 and 4, with respect to the evaluation point "partition wall thickness", the partition wall thickness during centrifugation is slightly insufficient. Thus, it may not be possible to form a partition wall having sufficient strength when serum or plasma is separated.

In Comparative Examples 1 and 2, both the evaluation points "flowing" and "partition wall thickness" are severely deteriorated in comparison with those of Examples 1 to 21 and Reference Examples 1 to 5. Thus, it is not possible to maintain the thixotropy over a prolonged period due to overtime changes. Moreover, it is not possible to form a partition wall having sufficient strength when serum or plasma is separated.

The invention claimed is:

1. A serum- or plasma-separating composition comprising a resin composition having viscosity of 10 to 200 Pa·s at 25° C., a silica fine powder, and an amide-based compound represented by the following formula (1):

[Formula 1]

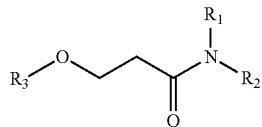

(1)

wherein $R_3$ is an alkyl group having 1 to 4 carbon atoms; and $R_1$ and R7 are independently a hydrogen atom or a linear or branched alkyl group having 1 to 8 carbon atoms and wherein the resin composition is at least one of a (meth)acrylic acid ester-based polymer, and a mixture of petroleum resin and a trimellitic acid-based plasticizer.

2. The serum- or plasma-separating composition according to claim 1, wherein the silica fine powder contains hydrophilic silica.

3. The serum- or plasma-separating composition according to claim 2, wherein the content of the hydrophilic silica is in the range of 1.40 to 2.00% by weight.

4. The serum- or plasma-separating composition according to claim 1, wherein the content of the amide-based compound is in the range of 0.10 to 0.35% by weight.

5. The serum- or plasma-separating composition according to claim 2, wherein hydrophobic silica is contained in addition to the hydrophilic silica.

6. The serum- or plasma-separating composition according to claim 5, wherein the total content of the hydrophobic silica and the hydrophilic silica is in the range of 1.40 to 2.50% by weight.

7. The serum- or plasma-separating composition according to claim 1, wherein the specific gravity of the serum- or plasma-separating composition is from 1.038 to 1.045.

8. A blood collection container containing the serum- or plasma-separating composition according to claim 1 therein.

* * * * *